US010112894B2

United States Patent
Hu

(10) Patent No.: US 10,112,894 B2
(45) Date of Patent: Oct. 30, 2018

(54) CYCLIC PROCESS FOR PRODUCING TAURINE

(71) Applicant: VITAWORKS IP, LLC, North Brunswick, NJ (US)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

(21) Appl. No.: 15/832,667

(22) Filed: Dec. 5, 2017

(65) Prior Publication Data

US 2018/0093946 A1    Apr. 5, 2018

Related U.S. Application Data

(63) Continuation-in-part of application No. 15/495,297, filed on Apr. 24, 2017, now Pat. No. 9,926,265, which is a continuation of application No. 15/366,798, filed on Dec. 1, 2016, now Pat. No. 9,815,778, which is a continuation-in-part of application No. 15/268,071, filed on Sep. 16, 2016, now Pat. No. 9,745,258.

(51) Int. Cl.
*C07C 303/02* (2006.01)
*C07C 303/32* (2006.01)
*C07C 303/44* (2006.01)

(52) U.S. Cl.
CPC .......... *C07C 303/02* (2013.01); *C07C 303/32* (2013.01); *C07C 303/44* (2013.01)

(58) Field of Classification Search
CPC .... C07C 303/02; C07C 303/32; C07C 303/44
See application file for complete search history.

(56) References Cited

U.S. PATENT DOCUMENTS

| | | | |
|---|---|---|---|
| 1,932,907 A | 10/1933 | Schmidt | |
| 1,999,614 A | 4/1935 | Schmidt et al. | |
| 2,693,488 A | 11/1954 | Sexton | |
| 2,820,818 A | 1/1958 | Britton | |
| 3,326,895 A * | 6/1967 | Coker | C07D 203/08 548/954 |

(Continued)

FOREIGN PATENT DOCUMENTS

| CN | 101486669 A | 7/2009 |
|---|---|---|
| CN | 101508657 A | 8/2009 |

(Continued)

OTHER PUBLICATIONS

Chem, W. et al., The process of Preparation of Tarine from ethylenimine, 2011, Zhejiang Chemical Industry, vol. 42, No. 5, English abstract 1 page (Year: 2011).*

(Continued)

*Primary Examiner* — Yate' K Cutliff
(74) *Attorney, Agent, or Firm* — Myers Wolin, LLC

(57) ABSTRACT

There is disclosed a process for producing taurine from aziridine by (a) adding gaseous aziridine or a solution of aziridine to a solution of ammonium bisulfite, or ammonium sulfite, or a mixture of ammonium bisulfite and ammonium sulfite to form ammonium taurinate; (b) decomposing ammonium taurinate by heating and removing ammonia from (a) to obtain a crystalline suspension of taurine; and (c) separating taurine by means of solid-liquid separation.

4 Claims, 2 Drawing Sheets

(56) References Cited

U.S. PATENT DOCUMENTS

| | | | |
|---|---|---|---|
| 5,646,320 | A | 7/1997 | Cassady et al. |
| 5,739,365 | A | 4/1998 | Briody et al. |
| 8,609,890 | B1 | 12/2013 | Hu |
| 9,061,976 | B1 | 6/2015 | Hu |
| 9,108,907 | B1 | 8/2015 | Hu |
| 9,428,450 | B2 | 8/2016 | Hu |
| 9,428,451 | B2 | 8/2016 | Hu |
| 9,573,890 | B2 | 2/2017 | Hu |
| 9,593,076 | B2 | 3/2017 | Hu |
| 9,598,357 | B1 | 3/2017 | Hu |
| 9,745,258 | B1 | 8/2017 | Hu |
| 9,815,778 | B1 | 11/2017 | Hu |
| 2015/0299113 | A1 | 10/2015 | Hu |
| 2015/0299114 | A1 | 10/2015 | Hu |
| 2016/0355470 | A1 | 12/2016 | Hu |

FOREIGN PATENT DOCUMENTS

| | | |
|---|---|---|
| CN | 101508658 A | 8/2009 |
| CN | 101508659 A | 8/2009 |
| CN | 101717353 A | 6/2010 |
| CN | 104945289 A | 9/2015 |
| CN | 105693559 A | 12/2015 |
| CN | 105732440 A | 7/2016 |
| CN | 106008280 A | 10/2016 |
| CN | 106588704 A | 11/2016 |
| CN | 107056659 A | 8/2017 |
| DE | 219023 A3 | 2/1985 |
| EP | 3284737 A1 | 2/2018 |
| JP | S63243066 A | 10/1988 |
| JP | H04352760 A | 12/1992 |
| JP | H108268995 A | 10/1996 |
| JP | 6227815 B2 | 11/2017 |
| JP | 2017206495 A | 11/2017 |
| JP | 2017533883 A | 11/2017 |
| WO | 0177071 A1 | 10/2001 |

OTHER PUBLICATIONS

Steuerle, U. et al., Aziridines, 2012, Ullmann's Encyclopedia of Industrial Chemistry, vol. 4, pp. 515-522 (Year: 2012).*
Extended European Search Report, dated Feb. 13, 2018, including the European search opinion issued by the European Patent Office for corresponding European Patent Application No. 17187912.5.
Liu Fuming Process Design of the Ammonolysis Reaction of Taurine, China Chemical Trade, 2013, No. 8, pp. 120. (Original article is published in China in Chinese, an English translation by the Applicant is included).
Liu Fuming, Xie Liming Study of the Ammonolysis Reaction for Taurine, Shandong Chemical Industry, 2015, 44(5), pp. 27-28,30. (Original article is published in Chinese. An English translation by the Applicant is included).
Canada First Office Action dated Oct. 3, 2017, for corresponding Canada application No. 2,977,184.
Canada Notice of Allowance dated Nov. 20, 2017, for corresponding Canada application No. 2,977,184.
Japanese Notice of Reasons for Rejection, issued by the Japanese Patent Office dated Dec. 5, 2017 and English translation for corresponding Japan application No. 2017-159725.
Japanese Decision to Grant, issued by the Japanese Patent Office dated Jan. 31, 2018 for corresponding Japan application No. 2017-159725.
USPTO Non-Final Office action dated Mar. 23, 2017, for corresponding U.S. Appl. No. 15/268,071.
USPTO Final Office action dated Jun. 9, 2017, for corresponding U.S. Appl. No. 15/268,071.
USPTO Non-Final Office action dated Aug. 22, 2017, for corresponding U.S. Appl. No. 15/366,798.
Chen, W.R.; Lu, J.P.; Wen, J.H.,; Wang, J.F.; "The Process of Preparation of Taurine from Ethylenimine"; Zhejiang Chemical Industry, 2011, vol. 42, No. 5, pp. 5, 18-20.

* cited by examiner

CYCLIC PROCESS FOR PRODUCING TAURINE

CROSS REFERENCE TO RELATED APPLICATIONS

This application is a continuation-in-part of the co-pending application Ser. No. 15/495,297, filed on Apr. 24, 2017, which is a continuation-in-part of the co-pending application Ser. No. 15/366,798, filed on Dec. 1, 2016, now U.S. Pat. No. 9,815,778, which is a continuation-in-part application of Ser. No. 15/268,071, filed on Sep. 16, 2016, now U.S. Pat. No. 9,745,258, all of which are incorporated herein by reference.

TECHNICAL FIELD

The present invention relates to a cyclic process for the production of taurine from ammonium isethionate in a high overall yield (i.e., greater than 90% to nearly quantitative) by carrying out the ammonolysis reaction of alkali isethionate to alkali taurinate in the presence of a mixture of alkali ditaurinate and alkali tritaurinate, followed by reacting with ammonium isethionate.

BACKGROUND OF THE INVENTION

Taurine can be referred to as 2-aminoethanesulfonic acid and is one of the amino sulfonic acids found in the tissues of many animals. Taurine is an extremely useful compound with beneficial pharmacological effects, such as detoxification, fatigue-relief, and nourishing and tonifying effects. As a result, taurine finds wide applications as an essential ingredient for human and animal nutrition.

Taurine is currently produced in an amount of over 60,000 tons per year from either ethylene oxide or monoethanolamine. At the present time, most taurine is produced from ethylene oxide, following a three-step process: (1) the addition reaction of ethylene oxide with sodium bisulfite to yield sodium isethionate; (2) the ammonolysis of sodium isethionate to yield sodium taurinate; (3) the neutralization with an acid, i.e., hydrochloric acid and, preferably, sulfuric acid, to generate taurine and inorganic salts.

Although the ethylene oxide process is well established and widely practiced in commercial production, the overall yield is not very high, less than 80%. Moreover, the process generates a large waste stream that is increasingly difficult to dispose of.

The first stage of the ethylene oxide process, the addition reaction of ethylene oxide with sodium bisulfite, is known to yield sodium isethionate in high yield, practically quantitative, as disclosed in U.S. Pat. No. 2,820,818 under described conditions.

Therefore, the problems encountered in the production of taurine from the ethylene oxide process arise from the ammonolysis of sodium isethionate and from the separation of taurine from sodium sulfate.

U.S. Pat. No. 1,932,907 discloses that sodium taurinate is obtained in a yield of 80%, when sodium isethionate undergoes ammonolysis reaction in a molar ratio of 1:6.8 for 2 hours at 240 to 250° C. U.S. Pat. No. 1,999,614 describes the use of catalysts, i.e., sodium sulfate, sodium sulfite, and sodium carbonate, in the ammonolysis reaction. A mixture of sodium taurinate and sodium ditaurinate is obtained in a yield as high as 97%. However, the percentage for sodium taurinate and sodium ditaurinate in the mixture is not specified.

DD 219 023 describes detailed results on the product distribution of the ammonolysis reaction of sodium isethionate. When sodium isethionate undergoes the ammonolysis reaction with 25% aqueous ammonia in a molar ratio of 1:9 at about 280° C. for 45 minutes in the presence of sodium sulfate and sodium hydroxide as catalyst, the reaction products comprise 71% of sodium taurinate and 29% of sodium di- and tri-taurinate.

WO 01/77071 is directed to a process for the preparation of ditaurine by heating an aqueous solution of sodium taurinate at a temperature of 210° C. in the presence of a reaction medium. A mixture of sodium taurinate and sodium ditaurinate is obtained.

It is therefore concluded from the foregoing references that the ammonolysis of sodium isethionate invariably yields a mixture of sodium taurinate, sodium ditaurinate, and sodium tritaurinate. The percentage yield of sodium taurinate has not been more than 80%.

In order to obtain taurine from sodium taurinate, U.S. Pat. No. 2,693,488 discloses a method of using ion exchange resins involving a strongly acid ion exchange resin in hydrogen form, and then an anion exchange resin in basic form. This process is complicated and requires the use of a large quantity of acid and base to regenerate the ion exchange resins in each production cycle.

On the other hand, CN101508657, CN101508658, CN101508659, and CN101486669 describe a method of using sulfuric acid to neutralize sodium taurinate to obtain a solution of taurine and sodium sulfate. Crude taurine is easily obtained by filtration from a crystalline suspension of taurine after cooling. However, the waste mother liquor still contains taurine, sodium sulfate, and other unspecified organic impurities, which are identified as a mixture of sodium ditaurinate and sodium tritaurinate.

U.S. Pat. No. 9,428,450, U.S. Pat. No. 9,428,451, U.S. Pat. No. 9,573,890, and U.S. Pat. No. 9,598,357 overcome some of the problems in the known ethylene oxide process by inhibiting the formation of the byproducts of the ammonolysis reaction of alkali isethionate, alkali ditaurinate and alkali tritaurinate, and converting the byproducts into alkali taurinate. The overall yield of the cyclic process for producing taurine from sodium isethionate is increased to from 85% to nearly quantitative.

CN 104945289A and CN 105732440A describe recycling of the mother liquor, which contains sodium ditaurinate and sodium taurinate, during the ammonolysis of sodium isethionate in the production of taurine to increase the yield and to reduce discharge of waste.

U.S. Pat. No. 8,609,890 discloses a cyclic process of using isethionic acid or sulfur dioxide to neutralize alkali taurinate to producing taurine and to regenerate alkali isethionate. U.S. Pat. No. 9,108,907 further discloses a process of using isethionic acid prepared from ethanol to neutralize alkali taurinate to regenerate alkali isethionate. The aim is to reduce or eliminate the use of sulfuric acid as an acid agent in the production of taurine.

U.S. Pat. No. 9,061,976 discloses an integrated production scheme by using sulfur dioxide as an acid and by converting the byproducts of the ammonolysis reaction, alkali ditaurinate and alkali tritaurinate, to alkali taurinate. The overall production yield is increased to greater than 90% and alkali sulfate is eliminated from the production process. One drawback of this process is the use of gaseous sulfur dioxide, which imparts a slight smell on the product. Another significant drawback is that the taurine product from this process may contain trace amount of alkali sulfite which could be an allergen for certain people.

U.S. Pat. No. 9,593,076 discloses a cyclic process for producing taurine from isethionic acid in a high overall yield of greater than 90% to nearly quantitative, while generating no inorganic salt as byproducts. Similarly, CN 106008280A describes the use of isethionic acid to neutralize sodium taurinate and to regenerate sodium isethionate. However, the starting material, isethionic acid, is difficult to obtain commercially and is produced by a costly process of bipolar membrane electrodialysis of alkali isethionate.

CN 101717353A describes a process of preparing taurine by (1) reacting ethylene oxide with ammonium sulfite to yield ammonium isethionate and ammonia; (2) ammonolysis of the obtained product to ammonium taurinate; (3) acidifying with sulfuric acid to afford taurine. However, repeated attempts fail to produce any taurine under disclosed conditions.

JPS63243066 discloses a process of preparing taurine by reacting aziridine or ethyleneimine with an aqueous solution of sulfurous acid and adjusting the pH of the solution with a base. Because of limited solubility of sulfurous acid, the reaction is carried out under very dilute condition and the process is not economical.

JPH04352760 discloses a process of preparing taurine by absorbing gaseous aziridine with a solution of excess ammonium bisulfite or alkali bisulfite. Taurine or alkali taurinate is separated by distilling off water under vacuum and the product is isolated by washing with an alcohol.

JPH08268995 describes a cyclic process of preparing taurine from aziridine by first reacting aziridine with an excess of alkali bisulfite to form alkali taurinate, which is neutralized with sulfur dioxide to taurine and to regenerate alkali bisulfite. The direct contact of sulfur dioxide with taurine imparts a slight foul smell on the final product taurine.

Chen et al describe a method of preparing taurine by reacting aziridine with an excess of ammonium bisulfite (*Zhejiang Chemical industry*, 2011, Vol. 42, No. 5, pp 5, 18-20). However, the method gives only a moderate yield of about 75% and a large amount of mother liquor that is difficult to dispose of.

It is an object of the present invention to overcome the disadvantage of the known processes for the production of taurine and to provide, in addition, advantages, which will become apparent from the following description.

It is another object of the present invention to disclose a process for the production of taurine from ammonium isethionate in a high overall yield (i.e., greater than 90% to nearly quantitative) without generating any inorganic salt as byproduct.

The starting material, ammonium isethionate, can be readily and economically produced by reacting ethylene oxide with ammonium bisulfite according to prior art, e.g., U.S. Pat. No. 5,646,320 and U.S. Pat. No. 5,739,365.

According to the process of the present invention, a solution of alkali isethionate or regenerated alkali isethionate, alkali ditaurinate, and alkali tritaurinate is mixed with an excess of ammonia and is subjected continuously to the ammonolysis reaction to form a mixture of alkali taurinate, alkali ditaurinate, and alkali tritaurinate, in the presence of one or more catalysts. After ammonium isethionate is added to the ammonolysis solution, excess ammonia is removed to obtain a crystalline suspension of taurine in a solution of alkali isethionate, alkali ditaurinate, and alkali tritaurinate. Upon the solid-liquid separation of taurine, the mother liquor is directly recycled to the ammonolysis step.

The advantage of using ammonium isethionate as a starting material becomes apparent in that no isolation of alkali salt as a byproduct is necessary after the separation of crystalline taurine from the mother liquor containing alkali isethionate, alkali ditaurinate, and alkali tritaurinate. Moreover, the final product, taurine, does not contain any inorganic salt, such as alkali sulfate or alkali halide, as impurity.

DESCRIPTION OF THE INVENTION

The present invention relates to a cyclic process for the production of taurine from ammonium isethionate in a high overall yield of greater than 90% to nearly quantitative without generating any inorganic salt as byproduct.

The starting material, ammonium isethionate is produced by reacting ethylene oxide with ammonium bisulfite according to the following equation:

Ammonium isethionate, produced in a solution, can be used directly for the production of taurine. Preferably, ammonium isethionate is purified by concentrating the solution to obtain crystalline materials. When solid ammonium isethionate is used in the production of taurine, the quality of taurine produced is improved and almost no purge of mother liquor is required from the cyclic process.

The process according to the present invention starts with mixing a solution of alkali isethionate or regenerated alkali isethionate, alkali ditaurinate, and alkali tritaurinate, with an excess of ammonia. The presence of alkali ditaurinate and alkali tritaurinate in the reaction solution inhibits the formation of byproducts, increases the production yield, and greatly reduces or eliminates the waste discharge from the production process. The alkali metals are lithium, sodium, or potassium.

The ammonolysis reaction is carried out at a temperature from 160° C. to 280° C. under the pressure from autogenous to 260 bars for 1 to 6 hours.

After the ammonolysis reaction, excess ammonia is dispelled from the reaction solution and reclaimed for reuse. Ammonium isethionate is added to the ammonolysis solution before or after the removal of excess ammonia to react with alkali taurinates to yield alkali isethionate and ammonium taurinate.

Ammonium taurinate is decomposed to taurine by heating and removing ammonia from the solution. The temperature for decomposing ammonium taurinate is from 75° C. to 150° C., preferably from 90 to 120° C., most preferably from 95 to 110° C. Removal of ammonia released from the decomposition of ammonium taurinate can be carried out under reduced, normal, or increased pressure.

The amount of ammonium isethionate in relation to alkali taurinate in the ammonolysis solution can be from 0.1 to 10 on the molar basis. Preferably, the molar ratio is from 0.5 to 1.5, more preferably from 0.9 to 1.1, and most preferably from 0.95 to 1.05. When the ratio is lower than the equivalent, the final pH after ammonia removal tends to be higher than 7 and more taurine will remain in the solution. When the ratio is greater than equivalent, the final pH is in the desirable range of 5 to 6, but additional alkali hydroxide will be consumed during the ammonolysis stage.

The reaction of alkali taurinate formed in the ammonolysis stage with ammonium isethionate proceeds according to the following equation:

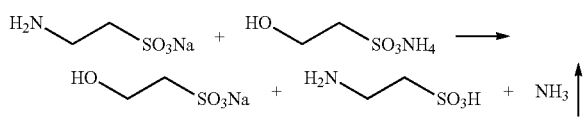

After complete removal of ammonia, the strongly basic solution becomes neutral to yield a crystalline suspension of taurine in a solution of alkali isethionate, alkali ditaurinate, and alkali tritaurinate. The final pH can also be fine-adjusted with the mixed acids of isethionic acid and ditaurine, produced by the bipolar membrane electrodialysis of the mother liquor containing alkali isethionate and alkali ditaurinate. The initial suspension is optionally concentrated, then cooled to crystallize taurine in a solution of alkali ditaurinate, alkali tritaurinate, and alkali isethionate. Taurine is obtained by means of solid-liquid separation.

After separation of taurine, the mother liquor, containing regenerated alkali isethionate, alkali ditaurinate, and alkali tritaurinate, is saturated with ammonia and is subjected to the ammonolysis reaction.

It becomes apparent that alkali in the reaction system is continuously recycled in the process and only ammonium isethionate is transformed to taurine. The net reaction of the cyclic process is:

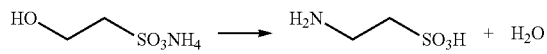

Useful and effective catalysts for the ammonolysis reaction are found among the alkali salts of hydroxide, carbonate, bicarbonate, hydrogen sulfate, sulfate, bisulfite, sulfite, nitrate, phosphate, chlorate, and perchlorate. Such salts are sodium hydroxide, lithium hydroxide, potassium hydroxide, lithium carbonate, lithium bicarbonate, sodium bicarbonate, sodium bicarbonate, potassium bicarbonate, lithium carbonate, sodium carbonate, potassium carbonate, lithium sulfate, sodium sulfate, potassium sulfate, lithium phosphate, sodium phosphate, potassium phosphate, lithium sulfite, sodium sulfite, and potassium sulfite.

The catalyst for the ammonolysis reaction of alkali isethionate in the presence of alkali ditaurinate and alkali tritaurinate can be one component or a combination of two or more components. Preferable catalysts are alkali hydroxide and the most preferable catalyst is sodium hydroxide.

The amount of catalyst used is not limited, but is usually from 0.01 to 10 in molar ratio of the catalyst to alkali isethionate. The ratio is preferably in the range of 0.01 to 1, more preferably 0.1 to 0.5, most preferably 0.2 to 0.3. A suitable amount of catalyst can be selected by those skilled in the art for the ammonolysis reaction to complete in desired time.

As a catalyst, alkali hydroxide is introduced into the reaction system and additional ammonium isethionate is required to neutralize the strong base. The result is an increased accumulation of alkali in the cyclic process. It is thus preferable to generate the alkali hydroxide within the production unit. A convenient way is to split a mixture of alkali isethionate and alkali ditaurinate in the mother liquor into an acidic component, a mixture of isethionic acid and ditaurine, and an alkali hydroxide component, by using bipolar membrane electrodialysis. The mixed acidic solution of isethionic acid and ditaurine is used as an acid after the ammonolysis while alkali hydroxide is used as a catalyst for the ammonolysis reaction.

The cyclic process according to the present invention affords taurine in a yield of greater than 90%, to nearly quantitative, and generates no waste other than a small amount of purge from the cyclic system.

Moreover, the taurine product produced according to the present invention does not contain any inorganic contaminants, such as alkali sulfate or alkali halide, which is present in the commercially available products from existing industrial processes.

Aziridine undergoes a ring-opening reaction with sulfurous acid or a salt of bisulfite or sulfite to form taurine or alkali taurinate, which is neutralized with an acid or an excess of bisulfite salts. The present invention discloses that ammonium taurinate, prepared by reacting aziridine with ammonium bisulfite, ammonium sulfite, or their mixture, can be decomposed to taurine by heating and removing ammonia from the reaction system, according to the following reaction:

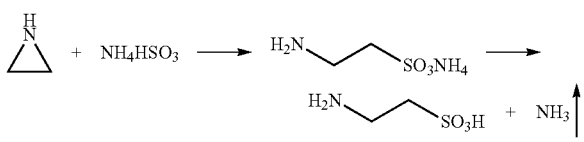

The process according to the present invention overcomes disadvantages in using sulfur dioxide, sulfurous acid, or an acid to produce taurine.

The reaction of aziridine with ammonium bisulfite, ammonium sulfite, or their mixture is highly exothermic and external cooling is necessary to maintain the reaction temperature from 0° C. to 100° C., preferably from 20° C. to 80° C., more preferably from 20° C. to 60° C., and most preferably from 25° C. to 45° C.

The aziridine, suitable for the present process, can be gaseous, neat liquid, or aqueous solution. The aziridine is prepared by gaseous dehydration of monoethanolamine in the presence of catalyst, by alkali hydroxide treatment of 2-aminoethylsulfonate ester, or by ammonolysis of 1,2-dichloroethane. Aziridine can be used in a purified form or as a crude product from the production process. Alkali hydroxide is selected from lithium hydroxide, sodium hydroxide, potassium hydroxide, or cesium hydroxide.

The molar ratio of aziridine to sulfite can be varied from 0.1 to 1, preferably from 0.5 to 1, more preferably from 0.8 to 1.0, and most preferably 0.9 to 0.95. A slight excess of sulfite is necessary for a complete reaction of aziridine to yield ammonium taurinate. Presence of even trace amount of aziridine in the reaction solution must be destroyed in the product stream of taurine as aziridine is quite toxic and carcinogenic to be a contaminant for a food product.

After the ring-opening reaction of aziridine with ammonium bisulfite is complete, ammonium taurinate is decomposed to taurine and ammonia by heating and the ammonia released from the reaction is expelled from the solution. Preferably, ammonia is absorbed with sulfur dioxide to produce ammonium bisulfite, which is used to react with aziridine. FIG. 2 illustrates the cyclic nature of the process according to the present invention.

After the separation of taurine by solid-liquid separation, the mother liquor is mixed with ammonium bisulfite, ammonium sulfite, or their mixture to prepare a solution to further react with aziridine. In addition, the mother liquor is also used to absorb ammonia and sulfur dioxide to prepare a solution of ammonium bisulfite, ammonium sulfite, or their mixture, which is then reacted with aziridine to complete the cyclic process. As the reaction between aziridine and sulfite generates negligible amount of byproduct, little purge of the mother liquor is required in the cyclic process.

The process according to the present invention yields taurine in a yield of greater than 90% to quantitative on the molar basis of aziridine.

The process according to the present invention can be carried out discontinuously, semi-continuously, and continuously.

EXAMPLES

Figure 1:
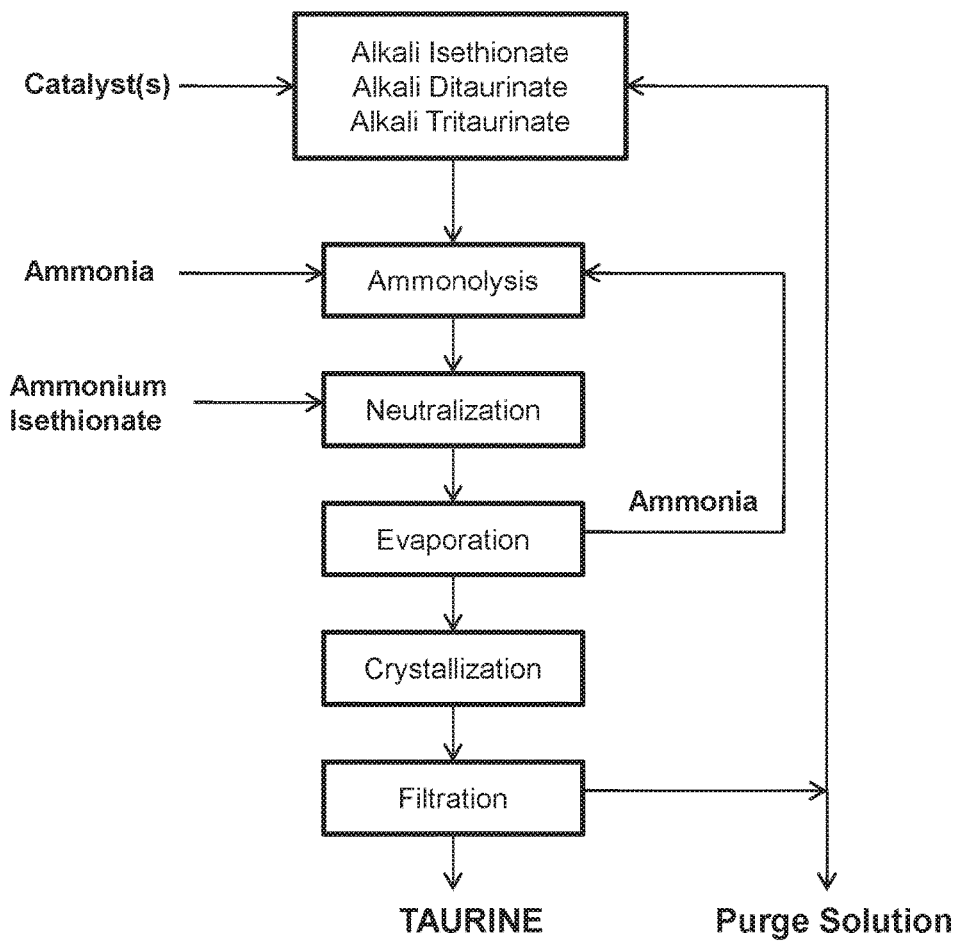
FIG. 1 illustrates one embodiment of a flowchart for producing taurine from ammonium isethionate.
Figure 2:
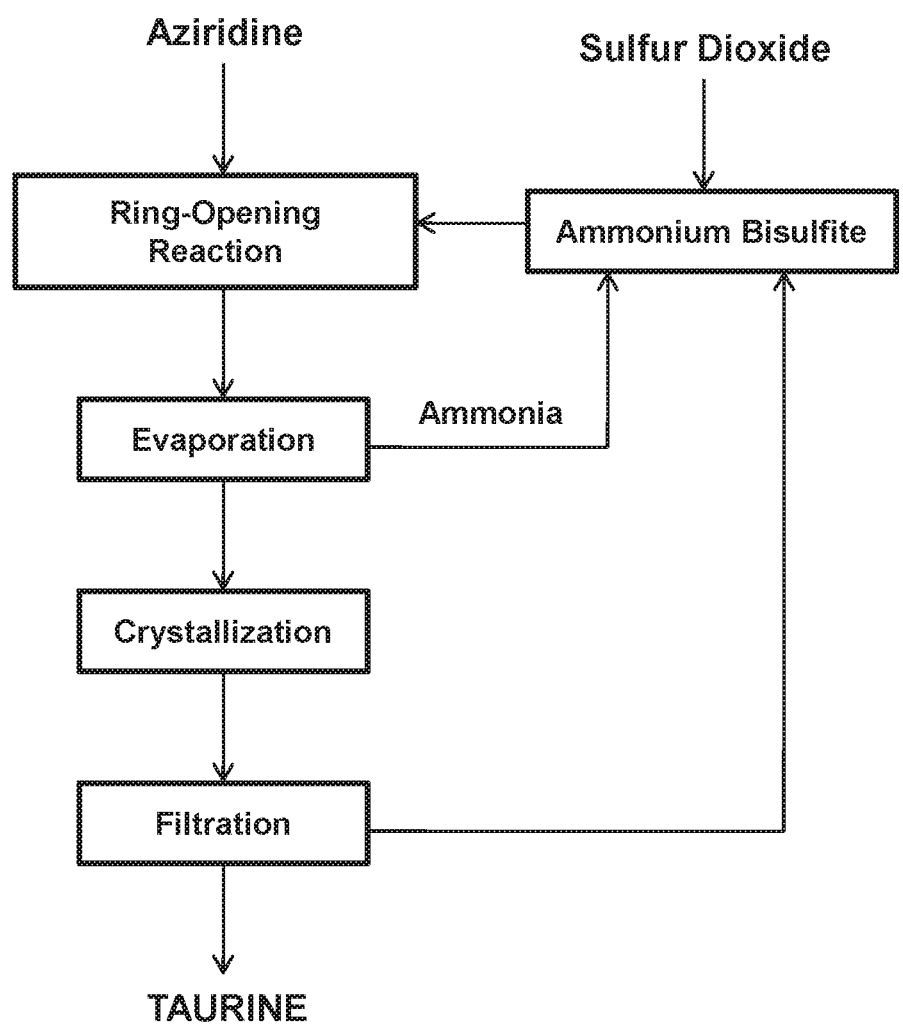
FIG. 2 illustrates one embodiment of a flowchart for producing taurine from aziridine.

The following examples illustrate the practice of this invention but are not needed to limit its scope.

Example 1

To a 2-L autoclave are added 1200 mL of 24% ammonia solution, 296 g of sodium isethionate, and 2 g of sodium hydroxide. The solution is heated to 260° C. for 2 hours under autogenous pressure. After cooling, 286.2 g of ammonium isethionate is added and ammonia is removed by boiling to bring the pH of the solution to pH 6.5. After heating to remove excess ammonia, concentrating and cooling to room temperature, a suspension of crystalline taurine is obtained. Taurine is recovered by filtration and dried to 189.3 g. Taurine is recovered in a yield of 75.7%.

Example 2

To the mother liquor of Example 1 is added 340 g of gaseous ammonia and total volume is adjusted to 1500 mL with deionized water, followed by addition of 12.4 g of sodium hydroxide. The solution is placed in a 2-L autoclave and is subjected to ammonolysis reaction and treatment with ammonium isethionate as described in Example 1.

Taurine, 241.2 g after drying, is obtained in a yield of 96.2% on the basis of ammonium isethionate used.

Examples 3 to 7

The mother liquor after isolation of taurine, after being saturated with ammonia, is repeatedly subjected to the ammonolysis reaction in the presence of 15 g of sodium hydroxide 5 times for an overall yield of taurine of 96.4% on the basis of ammonium isethionate used.

Example 8

To 240 g of a 50% solution of ammonium bisulfite was added dropwise 143.6 g of a 35% aqueous solution of aziridine, prepared by distilling a sodium hydroxide solution of 2-aminoethylsulfonate ester, while the temperature was maintained between 35 to 45° C. The initial pH of ammonium bisulfite was at 4.6 and the final pH of the solution became 9.8. After being stirred at the same temperature for 2 additional hours, the solution was heated to reflux to decompose ammonium taurinate to taurine and ammonia. After cooling, taurine crystallized from the solution and the pH of the crystalline suspension became 6.5.

After filtration and drying, 108 g of taurine was obtained as a white crystalline solid and 14 g of taurine remained in the mother liquor. The total yield was 97.6% on the basis of aziridine.

It will be understood that the foregoing examples, drawing, and explanation are for illustrative purposes only and that various modifications of the present invention will be self-evident to those skilled in the art. Such modifications are to be included within the spirit and purview of this application and the scope of the appended claims.

What is claimed is:

1. A process for producing taurine from aziridine, comprising:
   (a) adding gaseous aziridine or a solution of aziridine to a solution of ammonium bisulfite, or ammonium sulfite, or a mixture of ammonium bisulfite and ammonium sulfite to undergo a ring-opening reaction of aziridine to form ammonium taurinate;
   (b) decomposing ammonium taurinate to taurine and ammonia by heating and removing ammonia to obtain a crystalline suspension of taurine; and
   (c) separating taurine by means of solid-liquid separation to provide a mother liquor.

2. The process according to claim 1, wherein the mother liquor is combined with ammonium bisulfite, or ammonium sulfite, or a mixture of ammonium bisulfite and ammonium sulfite to prepare a solution to react with aziridine.

3. The process according to claim 1, wherein the mother liquor is used to absorb ammonia and sulfur dioxide to prepare a solution of ammonium bisulfite, ammonium sulfite, or a mixture of ammonium bisulfite and ammonium sulfite to react with aziridine.

4. The process according to claim 1, wherein the yield of taurine from aziridine is from 90% to quantitative.

* * * * *